US00PP25430P3

(12) United States Plant Patent

Klemm et al.

(10) Patent No.: US PP25,430 P3

(45) Date of Patent: Apr. 7, 2015

(54) *SOLIDAGO* PLANT NAMED 'KLESH13014'

(50) Latin Name: *Solidago hybrida*
Varietal Denomination: KLESH13014

(71) Applicant: Klemm+Sohn GmbH & Co. KG, Stuttgart (DE)

(72) Inventors: Per Klemm, Stuttgart (DE); Traude Mundinger-Flad, Magstadt (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 150 days.

(21) Appl. No.: 13/986,837

(22) Filed: Jun. 10, 2013

(65) Prior Publication Data

US 2014/0366236 P1 Dec. 11, 2014

(51) Int. Cl.
*A01H 5/00* (2006.01)

(52) U.S. Cl.
USPC ..... Plt./483

(58) Field of Classification Search
USPC ..... Plt./483
See application file for complete search history.

*Primary Examiner* — Annette Para
(74) *Attorney, Agent, or Firm* — James M. Weatherly; Barbara Campbell; Cochran Freund & Young LLC

(57) ABSTRACT

A new *Solidago* plant particularly distinguished by having a white ray floret color and early flowering is disclosed.

3 Drawing Sheets

Genus and species: *Solidago hybrida.*
Variety denomination: 'KLESH13014'.

BACKGROUND OF THE NEW PLANT

The present invention comprises a new and distinct variety of *Solidago,* botanically known as *Solidago hybrida,* and hereinafter referred to by the variety name 'KLESH13014'. 'KLESH13014' originated from an open pollination between the proprietary female *Solidago* variety 'SH-2007-123' (unpatented), having white flowers and an unknown male *Solidago* variety in an open field in Stuttgart, Germany.

In August 2008 the two *Solidago* parental lines, 'SH-2007-123' and an unknown *Solidago* line were crossed by open pollination in Stuttgart, Germany and seeds were obtained. The seeds were sown and plants were grown for evaluation. A plant line was selected in August 2009 and named 'KLESH13014'. In December 2009 'KLESH13014' was first vegetatively propagated in Stuttgart, Germany by tip cuttings. 'KLESH13014' was found to reproduce true to type in successive generations of asexual propagation via tip cuttings.

CROSS REFERENCE TO RELATED APPLICATIONS

Plant Breeder's Rights for 'KLESH13014' were applied for in Europe on Aug. 16, 2012, Application No. 2012/1776 and in Colombia on Jan. 2, 2013, Application No. A131788. 'KLESH13014' has not been made publicly available or sold more than one year prior to the filing date of this application.

SUMMARY

The following are the most outstanding and distinguishing characteristics of this new variety when grown under normal horticultural practices in Stuttgart, Germany.

1. White ray floret color; and
2. Early flowering.

DESCRIPTION OF THE PHOTOGRAPHS

This new *Solidago* plant is illustrated by the accompanying photographs. The photographs are of a plant twelve-weeks from planting grown in an open field in Stuttgart, Germany on Aug. 26, 2010. The colors shown are as true as can be reasonably obtained by conventional photographic procedures.

DESCRIPTION OF THE NEW VARIETY

Figure 1:
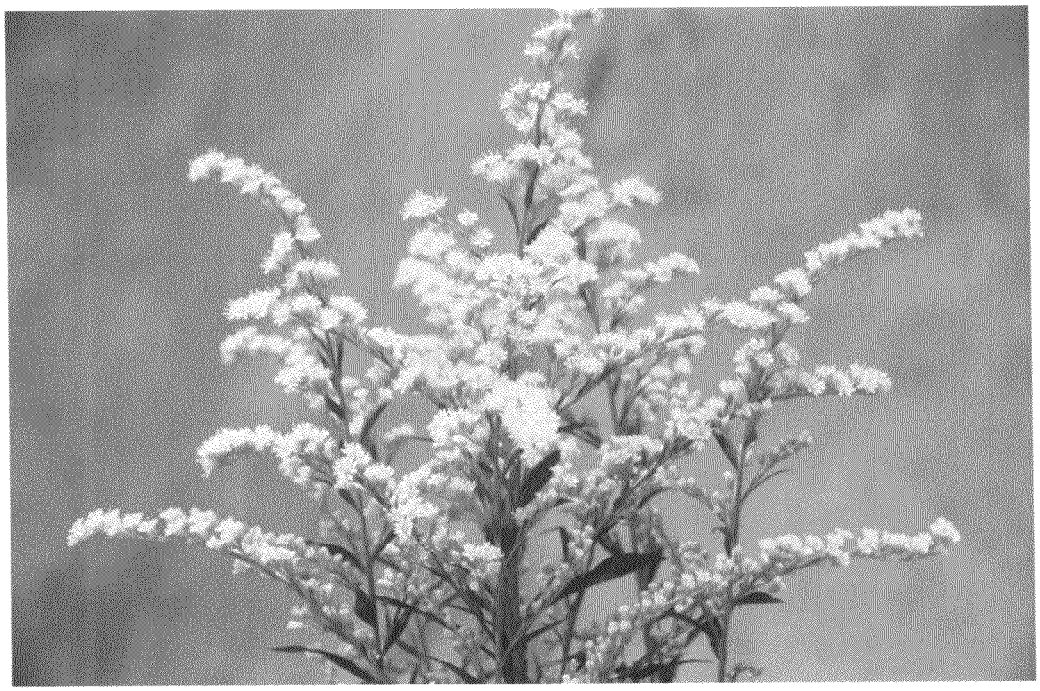
FIG. 1 shows the overall habit of the mature inflorescence of the plant.
Figure 2:
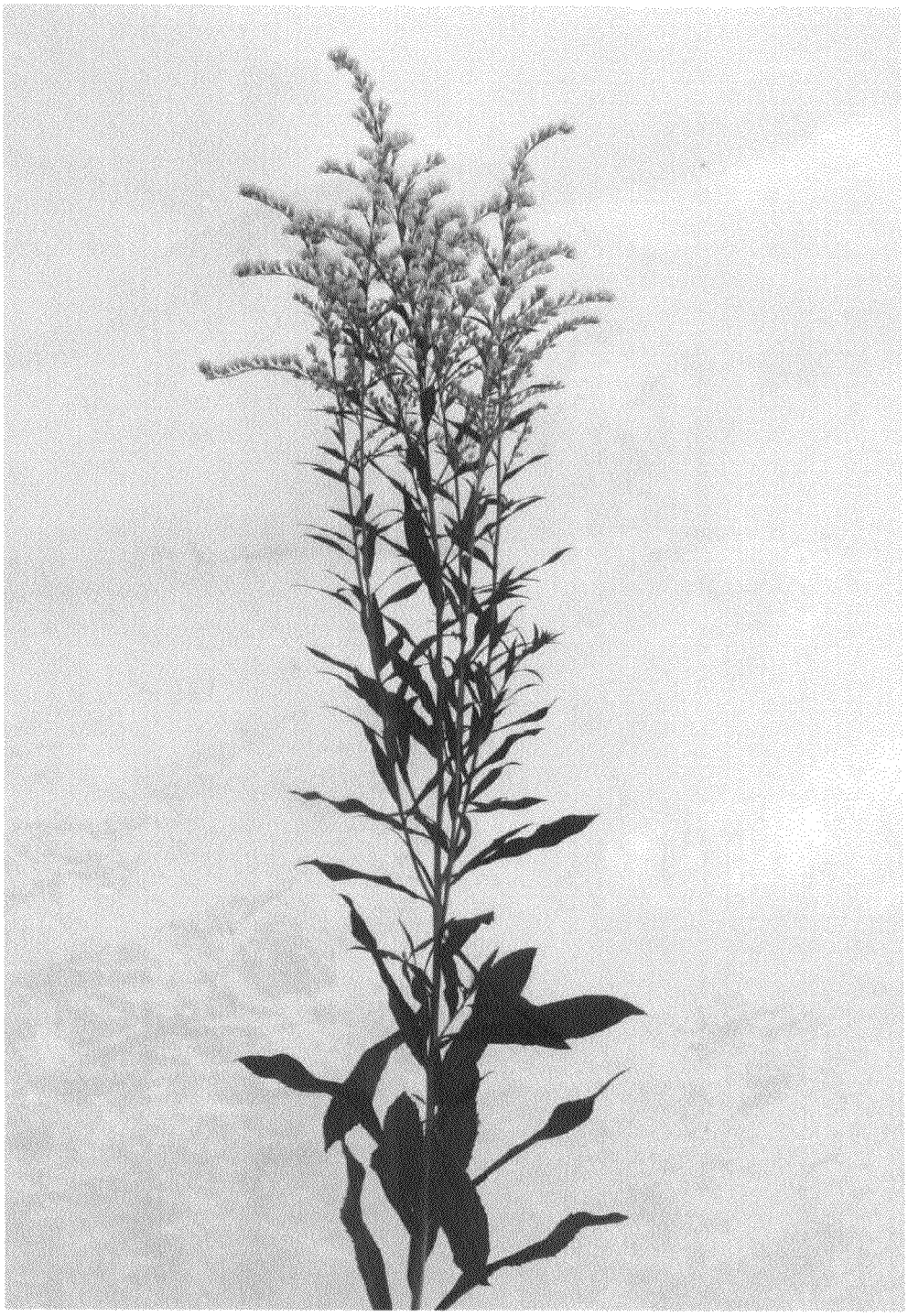
FIG. 2 shows the overall plant habit of the plant.
Figure 3:
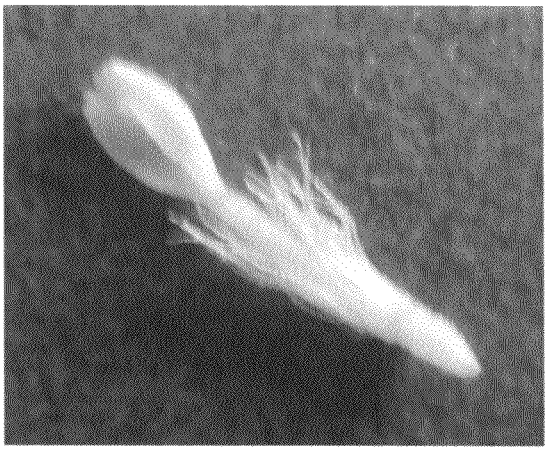
FIG. 3 shows a close-up of the ray floret of the plant.
Figure 4:
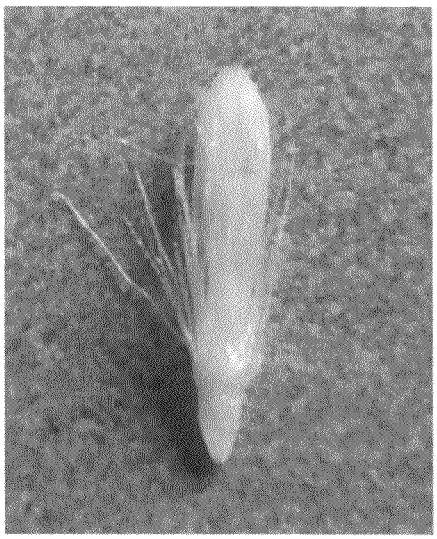
FIG. 4 shows a close-up of the disk floret of the plant.
Figure 5:
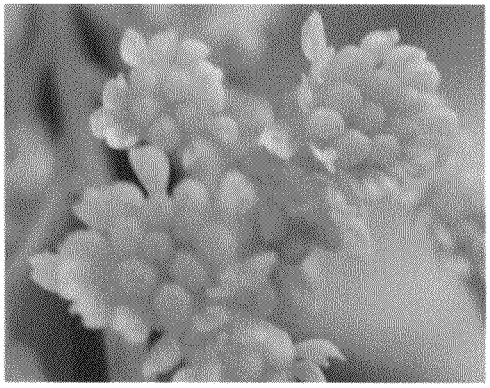
FIG. 5 shows a close-up of the inflorescence of the plant.

The following detailed descriptions set forth the distinctive characteristics of 'KLESH13014'. The data which define these characteristics were collected in Nairobi, Kenya on May 16, 2013. Data was collected on plants ten weeks after planting in a greenhouse with a plastic cover on a cloudy day with a temperature of 20° C. Color references are to The R.H.S. Colour Chart of The Royal Horticultural Society of London (R.H.S.), 4$^{th}$ edition (2001).

Classification:
- *Family.*—Asteraceae.
- *Botanical.*—*Solidago hybrida.*
- *Common name.*—Golden rod.
- *Designation.*—'KLESH13014'.

Parentage:
- *Female parent.*—Proprietary line 'SH-2007-123' (unpatented).
- *Male parent.*—Unknown.

Propagation:
- *Type.*—Tip cuttings.
- *Time to initiate roots.*—10 days in a special rooting area with controlled temperature and humidity: Day temperature 22° C., night temperature 20° C., 90 to 100% humidity.
- *Time to produce a rooted cutting.*—21 days with same conditions as time to initiate roots.
- *Root description.*—Fibrous root system.
- *Rooting habit.*—Freely branching.

Plant description:

*Plant form/growth habit.*—Perennial, upright, dense and bushy.

*Plant height.*—70.0 cm to 75.0 cm.

*Plant diameter.*—25.0 cm to 30.0 cm.

*Lateral branches.*—4 to 5 when pinched. Internode length: 4.5 cm to 5.0 cm. Strength: Sturdy. Texture: Pubescent. Color: RHS 146D.

Foliage description:

*Arrangement.*—Alternate.

*Length.*—14.0 cm.

*Width.*—2.5 cm.

*Shape.*—Lanceolate.

*Apex.*—Acute.

*Base.*—Acute.

*Margin.*—Shallowly toothed.

*Texture.*—Upper surface: Smooth. Lower surface: Smooth, veins protruding.

*Venation pattern.*—Midrib with secondary veins, netted.

*Color.*—Developing foliage, upper surface: RHS 137A. Developing foliage, lower surface: RHS 138B. Fully expanded foliage, upper surface: RHS 137B. Fully expanded foliage, lower surface: RHS 138B.

Inflorescence description:

*Appearance.*—Florets arranged in a panicle, forming a pyramidal flower head with slightly basipetal maturation.

*Flowering response.*—Under natural conditions, plants flower in late summer. At other times of year, flower initiation and development can be induced under short day conditions (less than 16 hours light). Response time is 10 weeks.

*Lastingness of the inflorescence.*—2 to 3 weeks in the field, 10 to 15 days in the vase as cut flower.

Inflorescence bud:

*Height.*—3.5 mm.

*Diameter.*—1.5 mm.

*Shape.*—Cylindrical.

*Color.*—RHS 144D.

*Spray height.*—50.0 cm.

*Spray diameter.*—27.0 cm.

Inflorescence size:

*Diameter.*—4.0 mm.

*Depth (height).*—5.0 mm.

*Diameter of disc.*—3.0 mm.

*Receptacle height.*—1.0 mm.

*Receptacle diameter.*—1.5 mm.

Ray florets:

*Number of ray florets per inflorescence/arrangement.*—13 florets, forming 1 row, single flower.

*Length.*—4.0 mm, therefrom 1.5 mm limb.

*Width.*—1.0 mm.

*Shape.*—Spoon shaped.

*Apex.*—Rounded.

*Base.*—Wedge shaped.

*Margin.*—Incised on the top.

*Texture.*—Upper surface: Smooth. Lower surface: Smooth.

*Color.*—When opening: Upper surface: RHS 155C. Lower surface: RHS 155C. Fully opened: Upper surface: RHS 155C. Lower surface: RHS 155C.

Disc florets:

*Arrangement.*—Clustered in a disk.

*Number of disc florets per inflorescence.*—6 to 10.

*Length.*—3.0 mm.

*Diameter, apex.*—1.0 mm.

*Diameter, base.*—0.5 mm.

*Shape.*—Club shaped.

*Apex.*—Obtuse.

*Color.*—Yellow. Immature: RHS 13B. Mature: RHS 13B.

Phyllaries:

*Quantity per inflorescence.*—10 to 13.

*Length.*—1.0 mm to 2.0 mm.

*Width.*—1.0 mm.

*Shape.*—Oblong.

*Apex.*—Acute.

*Base.*—Obtuse.

*Texture.*—Upper surface: Puberulent. Lower surface: Smooth.

*Color.*—Yellow-green. Upper surface: RHS 144D. Lower surface: RHS 145C.

Peduncles:

*Length, terminal peduncle.*—0.5 cm.

*Diameter.*—0.3 mm.

*Aspect.*—Flowers surrounding the panicle stems on peduncles, looking in all 4 directions, peduncle angle of 30°.

*Strength.*—Strong.

*Texture.*—Puberulent.

*Pubescent.*—RHS 145A.

Reproductive organs:

*Androecium.*—Present on disc florets only. Quantity per disc floret: 4 to 6. Anther shape: Elliptic. Anther length: 1.0 mm. Anther color: RHS 13B. Pollen amount: Moderate. Pollen color: RHS 13B.

*Gynoecium.*—Present on both ray and disc florets. Quantity per floret: 6 to 10. Pistil length: 1.0 mm. Stigma shape: Filamentous. Stigma color: RHS 158D. Style length: 1.0 mm. Style color: RHS 145A. Seed production: None observed.

Disease/pest resistance: Tolerant to powdery mildew and root rot.

Temperature tolerance: Tolerant to temperatures between −10° C. and 40° C.

COMPARISON WITH PARENTAL LINE AND KNOWN VARIETY

'KLESH13014' is a distinct variety of *Solidago* having a white ray floret color and early flowering. 'KLESH13014' is distinguished from its female parent as described in Table 1:

TABLE 1

Comparison with Parental Line

| Trait | Variety 'KLESH13014' | Female parent 'SH-2007-123' |
|---|---|---|
| Leaves | Length: 14.0 cm x Width: 2.5 cm | Length: 14.5 cm Width: 1.7 cm (more narrow) |

TABLE 1-continued

| Comparison with Parental Line | | |
|---|---|---|
| Trait | Variety 'KLESH13014' | Female parent 'SH-2007-123' |
| Spray length | 50.0 cm | 55.0 cm |
| Earliness | Early (10 weeks) | Late (12 weeks) |

'KLESH13014' is a distinct variety of *Solidago* having a white ray floret color. 'KLESH13014' is most similar to the *Solidago* plant named 'KLESH06001' (U.S. Plant Pat. No. 19,861). Differences between the two varieties are described in Table 2:

TABLE 2

| Comparison with Similar Variety | | |
|---|---|---|
| Trait | Variety 'KLESH13014' | Commercial line 'KLESH06001' |
| Ray floret color | White | Yellow |

We claim:

1. A new and distinct variety of *Solidago* plant named 'KLESH13014' as shown and described herein.

* * * * *